United States Patent [19]
Kowanko

[11] Patent Number: 6,036,918
[45] Date of Patent: Mar. 14, 2000

[54] VAPOR STERILIZATION

[75] Inventor: Nicholas Kowanko, Moorhead, Minn.

[73] Assignee: Enviro Medical Systems, Inc., Minneapolis, Minn.

[21] Appl. No.: 08/032,606

[22] Filed: Mar. 17, 1993

[51] Int. Cl.$^7$ ...................................................... A61L 2/20
[52] U.S. Cl. .............................................. 422/33; 422/37
[58] Field of Search ................................ 422/28, 33, 37; 252/106, 142

[56] References Cited

U.S. PATENT DOCUMENTS

| | | | |
|---|---|---|---|
| 3,383,163 | 5/1968 | Menashi | 422/23 |
| 4,296,068 | 10/1981 | Hoshino | 422/62 |
| 4,348,357 | 9/1982 | Bithell | 422/22 |
| 4,396,582 | 8/1983 | Kodera | 422/300 |
| 4,436,754 | 3/1984 | Jacobs | 424/333 |
| 4,447,399 | 5/1984 | Runnells et al. | 422/113 |
| 4,477,438 | 10/1984 | Willcockson et al. | 424/130 |
| 4,496,473 | 1/1985 | Sanderson | 252/186.41 |
| 4,512,951 | 4/1985 | Koubek | 422/23 |
| 4,518,585 | 5/1985 | Greene et al. | 424/130 |
| 4,521,375 | 6/1985 | Houlsby | 422/29 |
| 4,557,898 | 12/1985 | Greene et al. | 422/28 |
| 4,587,264 | 5/1986 | Jourdan-Laforte et al. | 514/557 |
| 4,613,452 | 9/1986 | Sanderson | 252/186.23 |
| 4,637,916 | 1/1987 | Hennenbert et al. | 422/295 X |
| 4,640,782 | 2/1987 | Burleson | 422/28 X |
| 4,642,165 | 2/1987 | Bier | 422/28 X |
| 4,687,635 | 8/1987 | Kaehler et al. | 422/26 |
| 4,738,794 | 4/1988 | Harrison et al. | 252/186.26 |
| 4,744,951 | 5/1988 | Cummings et al. | 422/28 |
| 4,757,014 | 7/1988 | Hendrickson et al. | 435/180 |
| 4,797,255 | 1/1989 | Hatanaka et al. | 422/28 |
| 4,801,427 | 1/1989 | Jacob | 422/23 |
| 4,818,888 | 4/1989 | Jacob | 422/23 |
| 4,956,145 | 9/1990 | Cummings et al. | 422/28 |
| 5,008,079 | 4/1991 | Wutzler et al. | |
| 5,084,239 | 1/1992 | Moulton et al. | |

FOREIGN PATENT DOCUMENTS

| | | |
|---|---|---|
| 0231632 | 8/1987 | European Pat. Off. . |
| 0269435 | 6/1988 | European Pat. Off. . |
| 2944278 | 5/1981 | Germany . |
| 1513266 | of 0000 | United Kingdom . |

OTHER PUBLICATIONS

Abstract: "Sterilization by formaldehyde and peracetic acid vapors", B. Tichacek, Cesk. Epidemiol, Mikrobiol., Immunol. vol. 29, 1980.

Abstract: "Studies on the sterilizing effect of gaseous peracetic acid on paper–wrapped material", M. Sproessig, H. Muecke, Pharmazie, vol. 31, 1976.

Abstract: "Halophilic bacteria susceptibility to peracetic acid vapor and ethylene oxide", P. Tash & B. Todd, Appl. Microbiol., 1973, vol. 25.

Abstract: "Apparatus for sterilization with peracetic acid vapors in the cold", R. Velecky & Z. Harna, Cesk. Hyg., 1969, vol. 14.

Abstract: "New results of a study of the disinfecting effects of activated formaldehyde vapor and Persteril", B. Tichacek & L. Ambroz, Cesk Epidemiol Mikrobiol Immunol., May 1983.

Abstract: "Devitalization of Bordetella bronchiseptica in vitro using vapors of Persterile and triethyl glycol", O. Doskocil & A. Fiser, Vet Med, Jun. 1979.

Abstract: "Peroxygens in Environmental Protection", Effluent and Water Treatment Journal, Jun. 1986.

Abstract: "Destruction of Bacterial Spores on Solid Surfaces", Journal of Food Processing and Preservation, 1980.

Abstract: Evaluation of Chemical Seed Coat Sterilants:, Plant and Soil, 1976.

"Design and Use of Novel Peracetic Acid Sterilizer for Absolute Barrier Sterility Testing Chambers", S.M. Davenport, Journal of Parenteral Science and Technology, 1989, Jul./Aug., vol. 43, No. 4.

"Stability of *Bacillus Subtilis* Var. Niger (Morphotype Globigii) Spores on Various Carrier Materials", Kimberly J. Rohn, PMA Seminar, Validation of Sterile Manufacturing Processes, Biological Indicators, Feb. 25–27, 1980.

"Hydrogen Peroxide and Other Oxidant Disinfectants", F. J. Turner, Ph. D., Disinfection, Sterilization, and Preservation, Third Edition, Lea & Febiger, 1983.

"Preservation and Storage of High–Moisture Grain With Propionic Acid", D.R. Hicks, H.G. Johnson, H.A. Cloud, C.M. Christensen and R.A. Meronuck, Agricultural Extension Service, University of Minnesota Agronomy No. 29 Revised 1975.

"Gaseous Sterilization", C.R. Phillips, Reprinted from Lawrence, C. A. Block, S.S.:Disinfection, Sterilization and Preservation, Lea & Febiger, 1968.

"Peracetic Acid Aerosols", Dr. Frank P. Greenspan, Manager, Organic Research and Development, Becco Chemical Division, Food Machinery and Chemical Corporation, Buffalo, N.Y.; Montfort A. Johnsen, Director of Research, Peterson Filling and Packaging Company, Danville, Illinois; Philip C. Trexler, Assistant Director, The Lobund Institute, University of Notre Dame, Notre Dame, Indiana, Publication Unknown, Prior Art.

(List continued on next page.)

*Primary Examiner*—Elizabeth McKane
*Attorney, Agent, or Firm*—Nikolai, Mersereau & Dietz, P.A.

[57] ABSTRACT

The present invention discloses the use of peracid vapor as a sterilant. A process is disclosed for sterilizing a load by exposure to peracid vapor, the load being disposed in a sterilization chamber adapted to contain the peracid vapor, including the steps of exposing the load to the peracid vapor in the sterilization chamber at reduced pressure, i.e., below atmospheric pressure and introducing a quantity of another gas, the gas being of a type which does not interfere with the sterilization procedure, to increase the pressure in the chamber to a value above that at which the chamber was when the peracid vapor alone was present but below atmospheric pressure, whereby the penetration of any vapor penetrable portions of the load to be sterilized by the peracid vapor is enhanced.

54 Claims, No Drawings

OTHER PUBLICATIONS

"Henry's Law Determinations for Aqueous Solutions of Hydrogen Peroxide, Methylhydroperoxide, and Peroxyacetic Acid", John A. Lind and Gregory L. Kok, Journal of Geophysical Research, vol. 91, No. D7, pp. 7889–7895<Jun. 20, 1986.

"Synergistic Killing of Spores of Bacillus Subtilis by Peracetic Acid and Alcohol", S. Leaper, Journal of Food Technology (1984), 19–355–360.

"Influence of Temperature on the Synergistic Sporicidal Effect of Peracetic Acid Plus Hydrogen Perioxide on Bacillus Subtilis SA22 (NCA 72–52)", S. Leaper, Food Microbiology, 1984–203.

"Performic and Perpropionic Acids As Disinfectants In Compairson With Peracetic Acid", V. Merka, F. Sita, V. Zikes, Journal of Hygience, Epidemiology, Microbiology and Immunology, 1985.

"Uber die Eignung der Peressigsaure zur Kalsterilisation", M. Sprossig, Wissenshaftliche Zeitschrift Der Universitat Rostock, 271–273 (1970).

"Sporicidal Effect of Peracetic Acid Vapor," Dorothy M. Portner and Robert K. Hoffman, Applied Microbiology, Nov. 1968, pp. 1782–1785, vol. 16, No. 11.

"Investigation of Vapor Phase Peracetic Acid on Materials Wrapped in Paper", M. Sprossig and H. Muoke, Phamacia, vol. 31, H.7, 491–402, (1976).

"Vapor Phase Hydrogen Perioxide Sterilization", James R. Rickloff, MS and Gary S. Graham, Ph. D., ETO Alternatives, p. 10–14, Jul. 12, 1989.

"Vapor Phase Hydrogen Peroxide Sterilization", R.K. O'Leary, J.H. Young, A.L. Cummings, P.A. Orelski, J.R. Rickloff, American Sterilizer Company, Erie, PA, Prior Art.

"Transfer Isolator to Protect Personnel from Exposure to Peracetic Acid", P.C. Trexler, Laboratory Animals (1979) 13, 163–165.

"Hospital Sterilization Using Ethylene Oxide—What's Next?", Stephen A. Conviser, ETO Alternatives, Jul. 12, 1989, pp. 3–14.

"Ozone as a Sterilizing Agent", Glen M. Stoddart, ETO Alternatives, Jul. 12, 1989, pp. 7–8.

"The Bactericidal, Fungicidal and Sporicidal Properties of Hydrogen Peroxide and Peracetic Acid", M.G.C. Baldry, Journal of Applied Bacteriology, 1983, 54, 417–423.

"Halophilic Bacteria Susceptibility to Peracetic Acid Vapor and Ethylene Oxide", Paul Tasch and Barbara Todd, Applied Microbiology, vol. 25, No. 2, Feb. 1973, pp. 205–207.

"A Flash Sterilizer Using Peracetic Acid", H. Bruce Cranford, Jr., US Army Medical Bioengineering Research and Development Laboratory, Report 7606, Prior Art.

"Comparison of the resistance to hydrogen peroxide of wet and dry spores of Bacillus subtilis SA22" by S. Leaper, Journal of Food Technology (1984)p695–702.

Design and Use of a Novel Peracetic Acid Sterilizer for Absolute Barrier Sterility Testing Chambers, S.M. Davenport, Technology Applications,, Sep. 5, 1989, pp. 22–10.

"Safe Handling of Peracetic Acid in a Closed Environment", J.P. Fordham, Laboratory Animals, (1978) 12, 247–248.

"Ozone Sterilization", Eskil L. Karison, D.Sc., ETO Alternatives, Jul. 12, 1989, pp. 8–14.

"Plasma Sterilization", Paul T. Jacobs, Ph.D., ETO Alternatives, Jul. 12, 1989, p. 13.

"Antifungal Properties of Performic and Perpropionic Acids", V. Merka, J. Dvorak, Journal of Hygience, Epidemiology, Microbiology, and Immunology, 1988.

"Disinfecting Properties of Performic Acid Against Bacteriophage 0 X 174 As A Model Of Small Envelope–Free Viruses", O. Bydzovska, V. Merka, Journal of Hygiene Epidemiology, Microbiology and Immunology 25, 1981, vol. 25, No. 4, 414–423.

"Disinfectants in Beet Sugar Extraction", Rolf Nystrand, Zuckerind 110 (1985) Nr. 8.

"Disinfection of Model Indicator Organisms in a Drinking Water Pilot Plant by Using Peroxone", Roy L. Wolfe, Mic H. Stewart, Sun Liang, and Michael J. McGuire, Applied and Environmental Microbiology, Sep. 1989, pp. 2230–2241.

"Automatic Control of Peracetic Acid Sterilization Solutions", J.W. Ogleby and J. Williams, Analytical Proceedings, Jun. 1985, vol. 22.

"Microwave Spectrum, Dipole Moment, and Substitution Structure of Peroxyformic Acid", M. Oldani, T.K. Ha, and A. Bauder, J. Am. Chem. Soc. vol. 105, No.3, 1983.

"Small–Molecule Chemisorption on NiSi2: Implications for Heterogeneous Catalysis", L.H. Dubois and R.G. Nuzzo, J. Am. Chem. Soc. 1982, 105, 365–369.

"Calormetric, H Nuclear Magnetic Resonance, and Molecular Orbital Studies of Hydrogen Bonding between Peroxy Acids and Oxygen Bases, Implications for Mono–oxygen Donation Potential of Peroxy Acids", Bozo Plesnicar, Viktor Menart, Milan Hodoscek, Jose Koller, Franci Kovac, and Joze Skerjanc, J. Chem. Soc, Perkin Trans, II 1986.

"Identification by ENDOR of Trp 191 as the Free–Radical Site in Cytochrome c Peroxidase Compound ES", Mohanram Sivaraja, David B. Goodin, Michael Smith, Brian M. Hoffman, Science, vol. 245, Aug. 18, 1989.

"Specific Expression of Nuclear Proto–Oncogenes Before Entry into Meiotic Prophase of Spermatogensis", Heineer Wolfes, Katsuhisa Kogawa, Clarke F. Millette, Geoffrey M. Cooper, Nature New Biology vol. 240 Nov. 8, 1972.

Rapid Removal of Peracetic Acid Fumes From Isolators, P.C. Trexler, Laboratory Animals, (1980) 14, 47–48.

"Cold Sterilization", Hans–Jurgen Ulrich, laboratory technician, Paul–Ehrich Institute, Frankfurt, West Germany, Publication Unknown, Prior Art.

"Desinfektion von Ionenaustauschern mit Peressigsauree (PES) Spezialqualitat 1A", Ueli boon Ballmoos, Zurricch und Heinz Soldavinni, Hanau, GAZ–EAUX–EAUX, usees 59 annee 1979 No. 11.

"Suitability of Peracetic Acid for Sterilization of Media for Mycoplasma Cultures", P. Wutzler, M. Sprossig, and H. Peterseim, Journal of Clinical Microbiology, Mar. 1975 pp. 246–249.

"Uber praktische Erfahrungen mit der Kalsterilisatiion von hitzelabilen Nahrmedien durch Peressigsaure", Von P. Wutzler, M. Sprossig und H. Mucke, Z. Med. Labortechnik 14 1973) pp. 157–162.

Abstract: "Alkalization of peracetic acid for surface disinfection to comply with occupational hygiene limits of room air", Wolfgang Geiler, Joerg Otto, Horst Muecke, Z. Klin. Med., 44–(4), 349–351, 59–5 (Air pollution and Industrial Hygiene), 1989.

Abstract: "Aqueous process for peracetic acid manufacture using phosphate triester absorbers", Georg Boehme, Willi Hofen, Guenter Prescher, Rainer Siegmeier, 45–4 (Industrial Organic Chemicals, Leather, Fats, and Waxes), 1988.

Abstract: "Action of chronic peracetic acid (Wofasteril) administration on the rabbit oral mucosa, vaginal mucosa, and skin", Paul Mueller, G. Raabe, J. Hoerold, U. Juretzek, Exp. Pathol. 34(4), 223–228.

Abstract: "Pharmacological actions of peracetic acid", Chenglin Li, Yuewi Ye, Jinju Deng, Zhiguo Zhang, Yaoxue Tongbao, 23(6), 345–8 1–5 (Pharmacology), 1988.

Abstract: "The synthesis of silica–supported phosphine and phospine oxide complexes of manganese(II) iodide and their reaction with sulfur dioxide", Brian L. Booth, Mu Guang Liu, Charles A. McAuliffe, J. Chem. Soc., Dalton Trans.,(6), 1415–17 78–7 (Inorganic Chemicals and Reactions), 1987.

Abstract: "Aqueous phase oxidation of sulfur(IV) by hydrogen peroxide, methylhydropeeroxide, and peroxyacetic acid", John A. Lind, Allan L. Lazrus, Gregory L. Kok, J. Geophys. Res., D. Atmos, 92(D), 4171–7 61–9 (Water), 1987.

Abstract: "Performic acid explosion", A. Oehlschlager, S. Ramaswamy, Ken Stuart, Chem. Eng. News, 65(15)W 59–5 (Air Pollution and Industrial Hygiene), 1987.

Abstract: "Test results for an electroaerosol generator for disinfecting rooms", M.N. Belov, L. Visnapuu. E. Parnaste, Tartu Riikliku Ulik. Toim, 707, 115–22 59–6 (Air Pollution and Industrial Hygiene), 1985.

Abstract: "Practically oriented representation of thermal safety limits for an indirectly cooled sime–batch reactor", Peter Hugo, Joerg Steinbach, Chem.—inc.–Tech, 57(9), 780–2 59–5 (Air Pollution and Industrial Hygiene), 1985.

Abstract: "Peracetic acid aerosol effect in long–term use of low germicidal concentrations on experimental animals", Wolfgang Heinze, Herbert Nattermann, Wiss. Z. Humboldt—Univ. Berlin, Math.—Naturwiss, Reihe, 33(5),513–517 4–3 (Toxicology), 1984.

Abstract: "Mechanism and limits of the detrimental effect of peracetic acid, lactic acid and acetic acid aerosols and of peracetic acid and sulfur dioxide gases on mammals", Wolfgang Heinze, Thomas Hahn, Gerold Wrensch, Anne Rose Fisher, Wiss. Z. Humboldt—Univ. Berlin, Math.—Naturwiss. Reihe, 31(6), 549–555 4–3 (Toxicology), 1982.

Abstract: "Acute inhalation toxicity of peracetic acid aerosols in mice", Siegfried Krueger, Wiss Z. Humbolt—Univ. Berlin , Math.—Naturwiss. Reihe, 31(6),543–8 4–3(Toxicology), 1982.

Abstract: "Determining acetic acid levels in the atmosphere", G.M. Shmuter, I.P. Kozyarin, V. Zh. Ratushnaya, V.G. Sukk, V.G. Cheerkasov, A.A. Maslenko, Gig. Sanit. (12), 31 59–1 (Air Polllution and Industrial Hygiene), 1984.

Abstract: "Effect of aerosols of peracetic acid on the microclimate of a section of the sow pig sty at a pig raising complex", V.F. Startsev, Donskois—Kh. Inst., (Sb. Nauchn. TR), (Ssoversh, Tekhnol, Proizvod, Svininy Govvyadiny), 78–81 59–6 (Air Pollution and Industrial Hygiene), 1982.

Abstract: "Toxic effects of peracetic acid. I. Morphopathological study on the skin an mucosa of guinea pigs under forced inhalation conditions", C. Bulnes, Goergina Garcia, Lidia Tablada, Rev. Salud Anim., 4(2), 75–84 4–3 (Toxicology), 1982.

Abstract: "Subacture and subchronic percutaneous tolerance tesing (28–day and 90–day test) of epicutaneously applied disinfectants as demonstrated by the example of peroxyethanoic acid", A. Kramer, W. Weuffen, M. Bauer, Martina Bauer, W. Heinze, E. Werner, G. Lorenz, U. Grimm, K. Brachmann, Pharmazie, 37(1), 41–6 1–5 (Pharmacology), 1982.

Abstract: "Aerosol disinfection of railway passenger cars by peracetic acid solutions", Sh. I. Satdykov, N.S. Lebedeva, G. Ya. Pisarenko, Gig. Sanit., (3), 80–1 59–3 (Air Pollution and Industrial Hygiene), 1981.

Abstract: "Effect of peracetic acid aerosols and action in animals", W. Heinze, E. Werner, Anne rose Fischer, Montash. Veterinaermed.36(9), 343–349 4–3 (Toxicology), 1981.

Abstract: "Toxicological aspects of intermediate disinfection by peracetic acid", S. Krueger, G. Wilsdorf, Marion Bebenroth, Monatsh. Veterinaermed.,32(20), 785–788, 1977.

Abstract: "A new family of cycloaliphatic epoxy resins for electrical insulation", T. Kimura, M. Tokizawa, S. Nishizaki, H. Teratani, Proc. Electr./Electron.Insul.Conf., 12TH, 269–273. IEEE:New York N.Y. 37–3 (Plastics fabrication and Uses), 1975.

Abstract: "Study of inhalation toxicity or performic, peracetic and perpropionic acid in mice", V. Merka, R. Urban, J. Hyg, Epidemiol., Microbiol., Immunol., 29(1), 54–60 4–3 (Toxicology), 1976.

Abstract: "Oxygen–alkali treatment of ligneous materials. V. Recycle and reuse of a waste liquor in an oxygen–alkali, peracetic acid, and hydrogen peroxide bleaching sequence", Tomoaki Nishida, Kokki Sakai, Tamio Kondo, Kami Pa Gikyoshi, 29(12), 641–649 43–6 (Cellulose, Lignin, Paper, Other Wood Products), 1975.

Abstract: "Animal tolerance to peracetic acid. I. Experimental results following the application of peracetic acid solutions on the skin of pigs", Angela Busch, E. Werner, Moonatsh, Veterinaermed., 29(13), 484–4998 44–3 (Toxicology), 1974.

Abstract: "Effect of aliphatic peracids on the eggs of *Ascaris suum* in vitro", R. Radvan, I. Merka, Cesk. Hyg., 17(2/3), 91–2 3–4 (Biochemical Interactions), 1972.

Abstract: "Tissue tolerance and peracetic acid toxicity in relation to plastics", K. Brazdova, M. Dluhos, R. Verecky, G. Sekaninova, I. Taborsky, V. Zajicova, Scr. Med. 43(8) 323–327 14 (Toxicology), 1970.

Abstract: "Fungicidal action of peracetic acid", Hanna Krzywicka, Barbara Sadowska, Rocz., Patsw. Zaakl. Hig., 22(1), 99104 19 (Pesticides), 1971.

Abstract: " Peracetic acid–hydrogen peroxide solution for cleansing and sterilization of contact lenses," Jean Michael Laroche, 63–6 (Pharmaceuticals), 1987.

Abstract: "Action of peracetic acid on Trichophyton verruccosum in cattle facilities", Marisol Gonzalez, Elba Alverez, Rev. Salud Anim., 9(4), 277–279 5–2 (Agrochemical Bioregulators), 1987.

Abstract: "Keratin fiber disinfection", Jana Dudova, Ludmila Nermutova, Gabriela Vilova, Vladimir Wagner, 40–9 (Textiles and Fibers), 1986.

Abstract: "Renalin: qualifications as a dialyzer sterilant", LeRoy J. Fischbach, AAMI Technol. Anal. Rev., 10–85(Hemodialyzer Reuse: Issues Solutions), 15–19, 1985.

Abstract: "Peroxygens in environmental protection", J.A.L. Fraser, Effluent Water Treat. J., 26(5–6), 186–189, 60–0 (Waste Treatment and Disposal), 1986.

Abstract; "Solution for sterilizing and depyrogenizing stainless steel tubing and filters in a closed system", Dr. Franz Koehler, K. G. Chemie, 63–8 (Pharmaceuticals), 1983.

Abstract: Interaction between methanal–preserved implants and peroxyethanoic acid (peracetic acid), K.P. Wenzel, H. Muecke, Pharmazie, 37(3), 222 63–7 (Pharmaceuticals), 1982.

Abstract: "Use of chemical decomposition of organic materials and biological tissues for therapuetic purposes for sterilization with respect to microorganisms and viruses", Karl Theurer, 63–3 (Pharmaceuticals), 1981.

Abstract: "Destruction of bacterial spores on solid surfaces", Bong–Ho Han, Gunnar Schornick, Marcel Loncin, J. Food Process. Preserv., 4(1–2), 95–110 17–2 (Foods), 1980.

Abstract: "Further studies on the protection of metals against the corrosive action of diluted peracetic acid by the addition of certain phosphates", E. Muecke, Pharmazie, 34(9), 573 56–8 (Nonferrous Metals and Alloys), 1979.

Abstract: "Disinfection of ion exchangers with peracetic acid of special quality IA", Ueli Von Ballmoos, Heinz Soldavini, Gas, Wasser, Abwasser, 59(11), 487–8 61–5 (Water), 1979.

Abstract: "Medium for chemical sterilization of medical instruments and aids. Part 1.", Vladimir Merka, Bohumil Koubalik, Vojen. Zdrav. Listy, , 45(4), 149–150 63–8 (Pharmaceuticals), 1976.

Abstract: "Studies on the sterilizing effect of gaseous peracetic acid on paper–wrapped material", M. Sproessig, H. Muecke, Pharmazie, 31(7), 491–492 63–8 (Pharmaceuticals), 1976.

Abstract: "Cold sterilization of water–containing ointment gels and emulsions", Heinz Kuehn, Eckhard Thomas, 63–6 (Pharmaceuticals), 1975.

Abstract: "Attempts to reduce peracetic acid corrosion of iron, copper, brass, and bronze using phosphate", H. Muecke, Pharmazie, 30(4), 238–240, 56–8 (Nonferrous Metals and Alloys), 1975.

Abstract: "Tissue cultivation of infected gynecological tumors after sterilization with peracetic acid", W. Krafft, M. Sproess, H. Muecke, F. Marzotko, W. Priebsch, Arch. Geschwulstforsch., 43(2), 177–181 14–10 (Mammalian Pathological Biochemistry), 1974.

Abstract: "Practical experience with cold sterilization of heat–labile nutrient media by peracetic acid", P. Wutzler, M. Sproessig, H. Muecke, Z. Med. Labortech., 14(3), 157–162 10–13 (Microbial Biochemistry), 1973.

Abstract: "Hatching and raising gnotobiotic chicks", V.V. Sorokin, P.N. Koturanov, L.A. Saltykova, D. V. Dubrovskaya, A.V. Nikolaeva, Biol. Aktiv. Veshchestva Mikroorganiznov, No. 1, 112–115 18–13 (Animal Nutrition), 1970.

Abstract: "Peracetic acid as sterilizing agent for culture serum", H. Schweizer, M. Sproessig, H. Muecke, P. Wutzler, Nature (London), New Biol., 240(97), 61–2 9–1 (Biochemical Methods), 1972.

Abstract: "Suitability of peracetic acid for cold sterilization", M. Sproessig, Wiss. Z. Univ. Rostock, Math.—Naturwiss. Reihe, 19(3), 271–273 (Biochemical Interactions), 1970.

Abstract: "Sterilization of ion exchangers with peracetic acid", D. Zange, H.J. Bauer, Pharm. Prax., (11), 251–252 63 (Pharmaceuticals), 1971.

Abstract: "Properties of peracetic acid", Horst Muecke, Martin Sproessig, Wiss. Z. Humboldt—Univ. Berlin, Math—Naturwiss. Reihe, 1896), 1167–1170 23 (Aliphatic Compounds), 1969.

Abstract: "Decontamination of hen eggs by peracetic acid", H. Cihova, V. Bilek, K. Navrat, K. Svoboda, Cesk. Hyg. 249–256 17 (Foods), 1970.

Abstract: "Use of wofasteril for disinfection in the fermentation and beverage industry", Werner Schade, Manfred Moehring, Kurt Seidel, Lebensm.—Ind., 17(9), 337–341 16 (Fermentations), 1970.

Abstract: "Sterilization by formaldehyde and peracetic acid vapors", B. Tichacek, Cesk. Epidemiol, Mikrobiol., Imunol., 29(2), 111–118 5–2 (Agrochemicals), 1980.

Abstract: "Disinfectant properties of peracetic acid", V. Milojkovic, Mikrobiologija, 6(1), 145–149 63 (Pharmaceuticals), 1969.

Abstract: "Apparatus for sterilization with peracetic acid vapors in the cold", R. velecky, Z. Harna, Cesk. Hyg., 14(4–5), 170–172, 63 (Pharmaceuticals), 1969.

Abstract: "Stability of peracetic acid", V. Lepkova, L. Vesela, Acta Univ, Palacki. Olomuc., Fac. Med., 46, 93–98, 63 (Pharmaceuticals), 1967.

Abstract: "Apparatus and method for preparation and dilution of disinfectant solutions", Leonardus Lips, 47–3 (Appratus and Plant Equipment), 1988.

Abstract: "Generation and use of performic acid as an industrial disinfectant", Dirk Groenewegen, Philip John Hall, Vincent Martin, 5–2 (Agrochemical Bioregulators), 1987.

Abstract: "Continuous catalytic exposidation of olefinic double bonds with hydrogen peroxide and formic acid", Gerhard Dieckelmann, Klemens Eckwert, Lutz Jeromin, Eberhard Peukert, Udo Steinberner, 45–4 (Industrial Organic Chemicals, Leather, Fats, and Waxes), 1984.

Abstract: "1,2–Epoxy–5,9–cyclodecadiene", Gerhard Kaebisch, Rudolf Truebe, Hans Wittman, Siegfried Raupach, Horst Malitius, 27–2 (Heterocyclic Compounds (One Hetero Atom), 1981.

Abstract: "1,1,2,2–Tetrahydroperfluoro and their alcohol esters", Louis Foulletier, Andre Lantz, 23–7 (Aliphatic Compounds), 1981.

Abstract: "Sulfoxides", Harold M. Pitt, 23–11 (Aliphatic Compounds), 1974.

Abstract: "Performic acid", V. A. Smirnov, L.N. Velikanova, G.N. Soltovets, A.P. Tomilov, 23–16 (Aliphatic Compounds), 1973.

Abstract: "p–Isopropylphenol and p– and o–cresol", Francois Bourdin, Francois Chizat, Michel Constantini, Michel Jouffret, 25–10 (Noncondensed Aromatic Compounds), 1972.

Abstract: "Calorimetric proton nuclear magnetic resonance, and molecular orbital studies of hydrogen bonding between peroxy acids and oxygen bases. Implications for mono–oxygen donation potential of peroxy acids", Bozo Plesnicar, Viktor Menart, Milan Hodoscek, Joze Koller, Franci Kovac, Joze Skerjanc, J. Chem. Soc, Perkin Trans. 2, (9), 1397–405 22–10 (Physical Organic Chemistry), 1986.

Abstract: (Devitalization of Bordetella bronchiseptica in vitro using vapors of Persterile and triethyl glycol), O. Doskocil, A. Fiser, Vet Med (Praha), Jun. 1979, 24 (6) p343–50, ISSN 0375–8427.

VAPOR STERILIZATION

BACKGROUND OF THE INVENTION

1. Field of the Invention

This invention relates to a process for sterilization, using peracid vapors as the sterilizing agent. It particularly relates to the use of a peracid sterilant vapor capable of contributing a partial pressure of at least about 1 torr to the total vapor pressure achieved during vaporization of the peracid agent in the sterilizing environment during at least the initial stage of the sterilization process. A preferred acid is peracetic acid. The invention has utility generally in public health care areas, such as medicine, dentistry, and other health care delivery areas not only for sterilizing materials and equipment to be used on patients but also for decontamination and/or sterilizing waste, particularly medical waste, to be disposed of as well.

2. Description of the Related Art

The art described herein is not intended to constitute an admission that any patent, publication or other information referred to herein is "prior art" with respect to this invention, unless specifically designated as such.

Contact with high pressure steam is universally recognized as an effective method for bringing about sterilization and it is extensively used. However, the high temperatures of the process (120–132° C.) preclude its use with heat sensitive materials. Furthermore, high temperature steam is corrosive to some metals, notably cutting edges, thus further limiting usefulness of high pressure steam. These facts have contributed to the development of cold sterilization methods.

Cold sterilization is a term used collectively for a number of different procedures which effect sterilization at temperatures substantially below those of the steam process. In one form of cold sterilization, the object to be treated is brought in contact with a liquid sterilant formulation. Among the limitations of this procedure is that the sterilant must then be removed from the sterilized object, generally by extensive washing under sterile conditions. Also, steps must be taken to protect personnel and environment from the liquid sterilant, thereby increasing the cost and complexity of the process.

Another form of cold sterilization utilizes a sterilant in the gas phase. The most widely used gas sterilant is ethylene oxide (ETO). ETO is a very effective antimicrobial agent. It penetrates most materials well. It does not destroy the structural integrity of a wide range of device materials. Among its disadvantages is that it is highly flammable, even explosive. Flame retardants are generally incorporated into the ETO sterilant formulation, frequently to the extent of 88% or 90%. A common flame retardant for ETO is Freon 12, a substance believed to be involved in the destruction of the earth's ozone layer. Environmental concerns have brought about severe regulations in the use of Freon 12. Its availability for future use in sterilization is at best unlikely. Carbon dioxide has been proposed as an alternative to Freon 12, but its use introduces a number of new problems. Other alternatives have been considered, but none have been shown to be satisfactory to date. The use of ETO as a gas sterilant is further complicated by the fact that ETO readily polymerizes, forming undesirable films on equipment and the load to be sterilized, and that its emission or retention in the load poses serious health hazards. Careful monitoring and very long aeration times are required. As a consequence of the many problems surrounding the use of ETO, an alternative cold sterilant is eagerly sought by the industry.

Ozone, or more precisely, a mixture of oxygen and ozone, has been proposed as a gaseous sterilant. Such a mixture is generated as needed by passing an electric discharge through a stream of oxygen. The effectiveness of ozone as a biocide has been known for many years. It has been used in water purification and in treating air in confined spaces. Ozone is a highly reactive oxidizing agent and as such is not very selective as a sterilant. It attacks a number of structural materials, notably natural gum rubber, several metals and some common plastics during the course of sterilization. Its general usefulness as a cold sterilant has not been fully established.

Hydrogen peroxide in the vapor phase has recently been proposed for cold sterilization. Like ozone, hydrogen peroxide is a highly reactive oxidizing agent. It has been reported to attack cellulosic wrapping materials which are commonly used in sterilization, necessitating the use of special wrapping materials. Also, various materials in the load to be sterilized appear to be penetrated to different degrees, and surface contaminants consume unpredictable amounts of the sterilant vapor. Its general usefulness remains to be established.

Formaldehyde in various formulations was used fairly extensively as a fumigant, disinfectant and sterilant. Reported carcinogenicity has severely restricted its utility.

The use of peracids in liquid form as a sterilant is known. Some initial experimental work has also been done with peracetic acid vapor in which its sterilant effect has been noted. However, no one has yet provided a practical process for using peracid vapor in vapor sterilization.

SUMMARY OF THE INVENTION

A process has now been developed which provides an alternative to the sterilization methods described above and which is essentially free from the disadvantages inherent in past methods.

Briefly, this new process involves contacting the item to be sterilized with peracid vapors produced by the vaporization of a peracid, in most cases from a liquid solution mixture at relatively low temperatures (below the temperatures of steam and more fully defined hereinafter) and at reduced pressure, i.e., below atmospheric pressure. The sterilant vapors when used in the process are essentially free from any liquid and the temperatures of the process are below the temperature to which the item to be sterilized is heat sensitive.

The preferred equipment will comprise a sterilization chamber containing the load to be sterilized and a separate vaporization chamber containing a peracid vapor source such as a peracid containing/generating solution mixture. Peracid vapors are withdrawn from such a solution mixture under reduced pressure, i.e., by application of a vacuum. These vapors are allowed to enter the sterilization chamber, which is also maintained at an appropriately reduced pressure. An indirect vapor path connection between the two chambers is provided which is designed to remove any liquid droplets present in the vapor and to prevent passage of liquid to the load. The load is thus exposed to vapor only. A number of suitable techniques are available for removing liquids from vapor for the purpose of practicing the present invention. The choice of a particular technique will be dictated by the rate of vaporization, and by the volume and flow rate of the vapors in the particular appliance under consideration. A bent or angular conduit, or one containing one or more baffles may be suitable for small units, while a cyclone-type separator may be more appropriate for large units. These and other designs of liquid-vapor separators are well described in the literature and will be familiar to those skilled in the art.

In an important aspect of the present invention, the process involves the steps of reducing the pressure in the sterilization chamber to below 100 torr, preferably below 10 torr and most preferably below 1 torr, introducing the peracid sterilant vapor, and then increasing pressure in the sterilization chamber by the introduction of a non-interfering gas or vapor which promotes permeation of the load by the peracid vapor. The amount of the peracid sterilant vapor introduced is best defined by its partial pressure. An acceptable range is above 1 torr with the upper limit being the partial vapor pressure of the particular peracid used at the operating temperature. A preferred range is 10–15 torr but it can be higher or lower. The final chamber pressure after addition of the non-interfering gas or vapor is preferably within the range of 50–650 torr, 600 torr being preferred. After a time effective to provide sterilization, the vapor is removed from the sterilization chamber by evacuation and/ or air flushing. Any suitable gas other than air may be used for this purpose. All or any of these steps may be repeated. The sterilized item(s), i.e., the "load" may then be removed.

This use of a non-interfering gas in the sterilization cycle is an important feature of the invention. It not only promotes penetration of a porous load by the sterilant vapor, but greatly improves efficiency of sterilization. It is to be noted that the peracid sterilant vapor is preferably generated by withdrawing it from solution in the vaporization chamber. Low pressures are conducive to that step, preferably less than 1 torr. The vapor is then passed to the sterilization chamber which must be at an internal pressure below that of the vaporization chamber to enable effective transfer of the sterilant. At these low pressures vapors do not diffuse efficiently into the interstices of a porous load, and sterilization of such loads at low pressure is excessively slow or ineffective. Significantly higher pressures, typically above 100 torr, or even 600 torr, are needed to insure efficient permeation of porous loads by sterilant vapor. The difficulty posed by the divergent pressure requirements for vaporizing and dispersing sterilant vapors as opposed to the conditions for effective load permeation is overcome by the use of the non-interfering gas according to this invention. Such gas is typically added to the sterilization chamber after introduction of the sterilant vapor as exemplified and described below.

Some of the important concepts of the process may involve a combination of steps such as:

a) Generating inherently unstable peracid mixtures in situ;

b) Withdrawal of peracid vapor from such mixtures under reduced pressure;

c) Delivery of this vapor, generally under reduced pressure, and in appropriate amount, to a sterilization chamber;

d) Introduction of a non-interfering gas to enhance penetration of the load by the sterilant vapor mixture;

e) Allowing a contact time sufficient to achieve sterilization of the load;

f) Removal of residuals from the load under reduced pressure, preferably by use of the vacuum system utilized for vaporization earlier; and g) optional repetition of steps a–e as needed.

A peracid, as the term is used herein, refers to an organic acid containing the peroxy group —C(O)—O—O—H. This includes such acids as peracetic acid (peroxyacetic acid), performic acid (peroxyformic acid) and perpropionic acid (peroxypropionic acid) as well as others such as the perfluorinated peracids, particularly perfluoroperacetic acid, perfluoroperpropionic acid and perfluoroperbutyric acid.

Organic peracids tend to be unstable; their solutions decompose on standing and so have very limited shelf life. Peracetic acid is the only organic peracid which is commercially available: it is marketed as a 35% solution mixture containing stabilizers and other ingredients. Other organic peracids are prepared in solution immediately before use, or they are generated in situ for liquid phase reactions. There are no commercial sources of peracid vapors known at this time.

Although the sporicidal effect of peracetic acid vapor has been documented in research references, the present invention is the only available practical process allowing controlled delivery of peracetic acid vapor and other peracid vapors for purpose of carrying out sterilization.

Further, the present invention provides a practical general method for making available a supply of peracid vapors in a form suitable for conducting gas phase sterilization. For example, other peracids such as performic and perpropionic acids can be generated in the liquid form in situ and vaporized according to the teachings of the present invention and utilized for gas phase sterilization. These peracids have only been utilized as liquid sterilants heretofore. Other examples of suitable peracids or mixtures of peracids including perfluorinated peracids and mixtures which can be utilized according to the teachings of the current invention will be apparent to those skilled in the art.

Specifically, the present invention lends itself to the in situ generation of peracid vapors for the purpose of sterilization, said vapor being withdrawn from a liquid mixture containing said peracid(s). Generally such liquid mixtures are unstable and cannot be conveniently or safely stored or transported, but can be conveniently generated in situ. The invention therefore makes available a supply of peracid vapors for the purpose of sterilization which is not otherwise practically available.

Among the many advantages afforded by peracids as gas sterilants is that they are very highly effective. They can therefore be used in low concentration with all advantages pertaining thereto. They penetrate most loads readily and evenly. They are not strongly retained by load materials, and so are readily removed at the end of the process. They are compatible with most device materials under intended use conditions. They are neither selectively absorbed by nor destructive to cellulosic materials. This allows the use of conventional towels and other wrapping materials in the present process.

DESCRIPTION OF THE PREFERRED EMBODIMENTS

While this invention may be embodied in many different forms, there are described in detail herein specific preferred embodiments of the invention. The present disclosure is an exemplification of the principles of the invention and is not intended to limit the invention to the particular embodiments illustrated.

As indicated above, the present invention makes use of peracid vapors to sterilize various items. These items may include tools, packaged and unpackaged equipment for treatment of patients and may even consist of waste such as medical trash items to be sterilized prior to disposal.

In a preferred form of the invention, the peracid vapors are produced by the preferential vaporization of peracid from a liquid solution or mixture. For this purpose, the peracid utilized must be volatile to the extent, for practical purposes, that it can contribute a partial pressure of at least about 1 torr under conditions of use eg., from ambient temperatures to those of 40° C. and higher. Specifically, such a peracid should be of a nature and be present in a concentration so as to be capable of contributing a partial pressure of generally about 1 torr to the total vapor pressure achieved in the complete or partial vaporization of the liquid solution in which the sterilant agent is present for effective sterilization.

Peracetic acid is the preferred peracid for use in the process of this invention, although other peracids may be used as well. It is a milder oxidizing agent than ozone or hydrogen peroxide, yet has excellent biocidal properties, and so may be expected to be more selective in its activity thereby providing sterilization without material degradation of the item being sterilized. Peracetic acid has relatively high vapor pressure and so is easily vaporized. Peracetic acid is preferentially vaporized from a mixture containing both its parent, acetic acid, and peracetic acid. The reverse situation applies in a mixture of hydrogen peroxide and its parent, water. Hydrogen peroxide is the more difficult to vaporize. The presence of strong intramolecular hydrogen bonding in peracetic acid, and the concomitantly reduced intermolecular interaction, also results in a more even load penetration than is observed with strongly interacting sterilants like ETO and hydrogen peroxide. Peracetic acid is compatible with most common device materials, and is not tenaciously retained by them.

Finally, the health hazards of peracetic acid have been studied extensively. It has been shown not to be mutagenic, teratogenic, carcinogenic, or to produce tumors in test animals at liquid concentrations below 3%. It is therefore safe to use under vapor sterilization conditions. Peracetic acid is known to have excellent antimicrobial properties at temperatures substantially above and below room temperature, and its usefulness as a liquid sterilant has been demonstrated in a number of systems, particularly by workers in Europe. Thus, in liquid form, it has been used to sterilize objects such as contact lenses, bioprosthesis, pharmaceutical cream and ointment base, implants, dialysers, air purifiers and ion exchangers, and has also been used by the dairy and beverage industries, as well as in waste water treatment. Peracetic acid spray has been described as an effective disinfectant in animal husbandry, and aerosols of peracetic acid have been used in the production of gnotobiotic chicks and ducklings. Other suggested uses of peracetic acid include disinfection of rooms, railway cars, and of military personnel.

In contrast to the use of liquid solutions of peracetic acid for sterilization, the present invention uses peracetic acid vapor and other peracid vapors as the active principle in sterilization. As already noted, initial experimental work with peracetic acid vapor has commented on its ability to sterilize in vapor form.

In practicing one form of the present invention, an aqueous solution is provided containing a mixture of hydrogen peroxide, glacial acetic acid and sulfuric acid. Such a mixture forms peracetic acid in situ, and that mixture provides sufficient partial pressure of peracetic acid to serve as an effective vapor source for practicing the invention. The peracid vapor may be obtained by partially or completely vaporizing the solution containing the peracid in a vacuum chamber or the like under reduced pressure.

Sources of peracid sterilant vapor are for example:
a) Peracetic acid 35% solution (may be diluted to 10 or 15%)
b) in situ generated peracetic acid
c) in situ generated performic acid from 30% hydrogen peroxide, formic acid and sulfuric acid
d) in situ generated perpropionic acid (as in c above)
e) in situ generated perfluorinated peracids.

Peracetic acid as commercially available in 35% solution is presently the most preferred source of peracid vapor. This solution is partially vaporized in a vaporization chamber under reduced pressure to provide the sterilant vapor. Perfluorinated peracids may be readily generated from the appropriate anhydride.

A number of advantages are realized by operating under reduced pressure, i.e., less than atmospheric. Vaporization of the sterilant is facilitated and can be achieved quickly and conveniently at relatively low temperatures, i.e., below 100° C., and preferably below 70° C. This is of particular advantage when vaporizing peracids which typically decompose at temperatures below their boiling points at atmospheric pressure. Also, at a given temperature, peracids decompose more slowly under reduced pressure and are available longer to carry out sterilization. Since vaporization and sterilization can be accomplished below atmospheric pressures at relatively low temperatures the useful life of the highly reactive peracetic acid molecules will be increased thereby increasing their effectiveness in the process of sterilization. Further, lower temperatures and pressures decrease the opportunity for undesirable side reactions and eliminate the hazards normally associated with the use of peroxides. No hazard is encountered when peracetic acid vapors are generated and used under the conditions described in the embodiments of this invention.

Reduced pressure operation greatly facilitates the tasks of introducing chemicals, and of trapping or removing volatiles which remain. Thus emission is effectively controlled and residuals are easily reduced to acceptable levels. As will be seen from preferred embodiments described below, the reduced pressure can be generated through any of a number of devices including aspirator devices, utilizing running water which can act as a diluent and sink for residuals. For small sterilizer units under use conditions, the quantities of chemicals used and the dilution achieved are such as to meet the requirements of regulatory agencies.

Another advantage of operation under reduced pressure, and one unique to this process, is that penetration of the load to be sterilized by the sterilant vapor and delivery of the sterilant into otherwise difficult to reach interstices can be conveniently enhanced by introducing a non-interfering gas such as air into the sterilizer chamber subsequent to vaporization. The absolute pressure in the chamber is thereby increased, facilitating entry of the sterilant into pores, lumens, and interstices and promoting permeation of the load by the sterilant. The addition of a non-interfering gas also improves heat transfer within the sterilization chamber, which is advantageous in some applications of the invention. Many non-interfering gases will suggest themselves for this purpose. Some examples are air, carbon dioxide, nitrogen and other inert gases such as argon.

In practicing the present invention in one preferred form, a solution containing peracid is vaporized under reduced pressure to provide the sterilant vapor. Typically, the reduced pressure for vaporization is below about 100 torr, preferably below about 10 torr and most preferably below about 1 torr. The peracid is preferentially vaporized from the solution. It is therefore not necessary to insure complete vaporization. Moreover, any less volatile ingredients can be left behind, and any potential side effect caused by such substances is avoided.

Another advantage of the invention is that vaporization is conducted in a chamber separate from the sterilization or working chamber. At least two benefits accrue from such practice. First, the operation of separate chambers under a different set of conditions can be facilitated. Thus, the advantage is offered of independently controlling the temperature of vaporization (sterilant gas generation) and of the actual sterilization of load. The vaporization chamber can be heated as required to aid vaporization without also heating a possibly heat sensitive load. For example, vaporization chamber may be smaller and held at 55° C. with a relatively high concentration of vapor and the sterilization chamber may be larger and held at 40° C. with a relatively low concentration of vapor. This is useful in handling loads of differing heat sensitivity with vapor from a common generating chamber or for providing vapor to several sterilization chambers simultaneously. It can be appreciated that a single vaporization chamber could be connected to a plurality of separate sterilization chambers and the generated vapors could be directed into each of them individually or simultaneously. This would find utility in an installation having large working chambers, such as bulk sterilization sites, and in which each working chamber might be filled with pallet loads of a single type of item requiring one set of conditions and still other sterilization chambers could be filled with pallet loads of some other materials or items requiring a different set of conditions.

Provisions allowing control over the composition of the vapors produced in the vaporizer can readily be made before they are allowed to enter the sterilizer and to contact the load. For example, the vapor generated in the vaporizer may be passed through a selective trap before being introduced into the sterilizer. The purpose of such a trap might be to remove an undesirable ingredient or ingredients from the vapor, or to decrease the concentration of such ingredient(s) in the vapor. Another purpose of the trap might be to remove droplets and to assure that only vapor (no liquid) passes to the load in the sterilizer chamber.

Yet another advantage of practicing the current invention is a reduction of metal corrosion. Such corrosion is known to be largely electrolytic in nature, requires water, and is equilibrium controlled. Under the conditions of the reduced pressure process, only trace amounts of adsorbed moisture are present on metal surfaces. Redox equilibrium would then be expected to be reached without a measurable consumption of metal, and no detectable corrosion would occur. Finally, it is well known that the efficacy of a number of gas sterilants, notably ETO, is dependent on the relative humidity. The process of the current invention is apparently not sensitive to variations in relative humidity, and no precautions need be taken to provide humidity under conditions of the process.

Further, maintaining the sterilization chamber below atmospheric pressure throughout the sterilization cycle provides a convenient safety feature, since the chamber door cannot be opened until the cycle is complete.

In a two chamber process of the invention, the steps of the most preferred embodiment are:
a) Evacuation of both vaporization chamber and sterilization chamber (the former being empty and the latter containing the load to be sterilized) to below 100 torr, and preferably below 10 torr, and most preferably below 1 torr;
b) Admitting to the vaporization chamber in appropriate amount an in situ generated solution containing peracid (s) (or a commercially prepared solution of peracetic acid);
c) Permitting vaporization of said solution to proceed while admitting the generated vapors to the sterilization chamber until the partial pressure of peracid vapor in that chamber is at least one torr, preferably higher, and most preferably about 10–15 torr;
d) Admitting another gaseous substance (gas or vapor which is non-interfering with the sterilization process) i.e., a non-interfering gas to the sterilization chamber to raise the absolute pressure in the chamber, preferably to about 600 torr or within an overall preferred range of about 50–650 torr, thereby enhancing penetration of a porous load by the sterilant vapor;
e) Allowing a contact time with the sterilant vapor long enough to achieve sterilization; generally this may be a few minutes to a matter of hours depending on the nature of the load;
f) Removal of sterilant and of other residuals from the load, preferably by evacuation and/or air flushing;
g) Optionally repeating any of steps a)–f);
h) Re-admitting air or any other suitable gas at the end of step f) to raise internal pressure of the sterilization chamber to ambient pressure and removing the load.
i) Removal of liquid residues remaining after the vaporization step c) above after each cycle, or at other intervals as dictated by use conditions.

Removal of residuals may be assisted by use of vacuum or by heating of the chambers in some circumstances.

While the invention is not to be limited thereto, it is believed that the mode of action of the peracid vapor in the present invention proceeds as discussed below. Peracetic acid is a strong oxidizing agent, and known to have a high affinity for sulfhydryl, sulfide, disulfide and carbon to carbon double bonds. These bonds play critical roles in the function of certain essential enzymes and of cell membranes. Oxidative cleavage of these bonds would in all probability inactivate the enzyme(s) in question and result in the death of the cell. Alternatively, if the affected bonds are part of the cell membrane, then the material transport and osmotic functions of the membrane would be disrupted, again causing death of the cell. Spore coats are known to have a high concentration of disulfide bonds. Disruption of the spore coat would expose the sensitive interior to the sterilant and cause spore death. The entire electron transport system of all living cells is highly susceptible to oxidation, and its disruption would result in rapid cell death.

In this context, it is interesting to note that most living cells protect themselves from oxidative damage with enzymes, such as catalase. Catalase very effectively decomposes hydrogen peroxide as soon as it is formed in cells as a result of radiation or some other process. Peracetic acid is not affected by catalase, and in fact deactivates this protective enzyme, and can therefore continue its action unhindered, while depriving the cell of an important protective mechanism. Further, alcohol, amine, and a variety of other functional groups abound in living cells. They are subject to oxidation by peracids such as peracetic acid, and the result of oxidation may well be fatal to the cells. Finally, peracids such as peracetic acid are powerful protein denaturants, and that effect will be lethal to all cells, microorganisms, and spores. The relative importance of these various effects will vary from one species to another. While the exact modality by which peracids kill microorganisms, spores, and viruses is not known, any of the mechanisms described above could alone cause death, and most if not all probably contribute in producing it.

The following examples will serve to illustrate, but not to limit, the invention. Unless otherwise noted, all parts and percentages are by weight.

SPECIFIC EXAMPLES

Organic peracid vapors were generated from solutions containing said peracids in accordance with the present invention and their effectiveness as gas phase sterilants was examined. It was found by direct experimental comparison that vapors of performic, peracetic and perpropionic acids (as well as mixtures of same) as well as perfluorinated peracids were more effective in bringing about spore death than was hydrogen peroxide alone. Also it was found that peracid vapors, when used under the conditions of the present invention, equaled and exceeded the published effectiveness of ETO.

Peracid vapors were found to meet and exceed the most stringent challenges proposed by the industry to evaluate gas phase sterilants, and they did so in a shorter process time than is required for ETO sterilization. Among these challenges may be listed the following:

1. Standard biological indicator strips in glassine envelopes, free or within multiple layers of fabric wrap;
2. Suture loops;
3. Stainless steel coupons, penicylinders and lumens;
4. Ceramic penicylinders;
5. Items 2–4 above inoculated in the presence of serum and hard water;
6. Plastic syringes contained within glassine envelopes and containing biological indicators strips (themselves sealed in glassine envelopes) inside the syringe barrel, and with the syringe plunger inserted.
7. All items 2–5 placed within a syringe as in 6 above. This challenge is more rigorous than any currently used in the industry.

A typical apparatus for conducting these evaluations consisted of a 28.3L stainless steel sterilization chamber which was connected to a 100 ml glass vaporization chamber. Connection was by means of a curved 1 cm by 10 cm Teflon tube arranged so as to allow vapor but not liquid to pass from one chamber to the other. A reservoir for admitting peracid containing liquid to the vaporization chamber was connected by means of a suitable valve and conduit. The temperatures of both chambers could be altered and maintained independently by means of conventional heaters, controls and monitoring devices. The entire system was connected to a vacuum pump capable of reducing the internal pressure to 10 torr or better, and pressure transducers were provided for monitoring chamber pressures. Air inlets were provided to both chambers, respectively. Provision allowing introduction and removal of load, article, or item to be sterilized were also present in the sterilization chamber.

Typical examples of evaluations using the above equipment follow.

EXAMPLE I

Commercial biological indicator strips containing about $10^6$ spores of accepted test organisms and sealed within glassine envelopes were placed within the sterilization chamber, exposed or wrapped in standard wrapping material commonly used in sterile packs. In this test the sterilization chamber was at 47° C. and the vaporization chamber at 62° C. The system was evacuated to less than one torr, the vacuum disconnected, and peracetic acid solution (4.0 ml, 35%, FMC Corp.) was introduced in the vaporization chamber. After 7 minutes of vaporization a pressure increase of about 12 torr was noted in the sterilization chamber, while some liquid remained in the vaporization chamber. Air was admitted to raise internal pressure to 633 torr. After 20 minutes the system was flushed by repeated evacuation.

EXAMPLE II

A mixture consisting of three parts 30% hydrogen peroxide, one part 90% formic acid, and a catalytic amount of concentrated sulfuric acid was prepared at room temperature within a few hours of use. (Such mixtures generate about 6% of performic acid in solution). A load including indicator strips was provided. The system was evacuated as in Example I above and 5.0 ml of the mixture was admitted to the vaporization chamber at 60° C. Vaporization was allowed to continue for 5 minutes at which time air was admitted to raise the internal pressure to 630 torr. After 40 minutes of sterilization time at 40° C. the system was flushed and opened as above.

EXAMPLE III

A solution containing perpropionic acid was prepared as in Example II above, but substituting propionic acid for formic acid. A load including biological indicator strips was provided. The system was evacuated to ca. 20 torr, and 5.0 ml of the solution was admitted to the vaporization chamber maintained at 65° C. After 5 minutes of vaporization air was admitted to raise internal pressure to ca.650 torr and the load was left in contact with the vapor at 40° C. for 42 minutes. The system was then flushed by repeated evacuation.

Following the sterilization cycles in Examples I–III, the spore test strips were recovered and incubated using standard procedures accepted in the industry and known to be appropriate for the test organisms. No bacterial growth was observed following seven days of incubation, indicating that effective sterilization of the loads had been achieved.

In all instances the total times required for the complete sterilization process were less than two hours. This is significantly shorter than the times required for ETO sterilization.

EXAMPLE IV

A mixture containing all three peracids was prepared as described in Example II. above, but using a 1:1:1 mixture of the parent acids. The load contained paper biological indicators, stainless steel penicylinders, stainless steel coupons, ceramic penicylinders and stainless steel lumens, all enclosed in glassine envelopes. The system was evacuated to ca 100 torr. 5.0 ml of the liquid mixture was admitted in to the vaporization chamber maintained at 65° C. Air was introduced to raise the pressure. Vaporization was allowed to proceed for 5 minutes, and evacuation and vaporization repeated twice more. After 58 minutes sterilization time at 40° C. the system was freed from residuals by repeated evacuation. Incubation of the test challenges in the load using standard methods showed no bacterial growth after seven days, consistent with effective sterilization.

EXAMPLE V

The load consisted of all biological challenges placed within a .syringe as described in #7 of the list of challenges set forth above. The system was evacuated to ca. 10 torr, while maintaining both the vaporization chamber and sterilization chamber at 25° C. Between 5 ml and 12.5 ml of peracid containing solution (commercial 35% peracetic acid or ca. 6% in situ generated performic, peracetic or perpropionic acid) was admitted to the vaporization chamber and allowed to vaporize for 5 minutes. Air was then admitted to raise the pressure to 650 torr. After 32 minutes of sterilization time the system was flushed by evacuation as usual. Incubation showed all items of the load to be sterile.

The following example illustrates the use of peroxyformic acid vapor for sterilization and shows the lower concentration limit thereof. It also illustrates a modified two-chamber process.

EXAMPLE VI

Six commercial biological indicator strips sealed in glassine envelopes and containing about one million spores each were placed in a commercial cassette holder designed to hold small instruments during sterilization. The cassette was placed in a 22.6 liter sterilization chamber maintained at 50° C. and the chamber evacuated to an absolute pressure of at least 10 torr. A liquid mixture designed to produce dilute peroxyformic acid was prepared by mixing together 1.0 milliliter of 30% hydrogen peroxide, 0.25 milliliter of 90% formic acid, and one drop of concentrated sulfuric acid. Ethyl alcohol (1.0 milliliter) was also added to the liquid mixture in order to increase the partial pressure of non-interfering materials. Such mixtures are known to generate about 6% peroxyformic acid in equilibrium with the other ingredients. After a short equilibration time, the liquid mixture was injected into a 50 mL vaporization chamber which was wholly contained within but separated from the sterilization chamber and allowed passage of vapors from one chamber to the other. The peroxyformic acid present rapidly vaporized, followed by vaporization of the major portion of the inactive ingredients. The latter provided sufficient additional pressure to facilitate penetration of the load. The calculated vapor pressure contribution by peroxyformic acid was 1.2 torr. The total pressure rise was 40 torr. After 30 minutes the chamber and contents were freed from residuals by evacuation. The test strips were then removed and incubated by standard procedures. No bacterial growth was observed after seven days.

In separate experiments neither formic acid (0.25 ml) nor hydrogen peroxide (1.0 ml, 30%) or ethyl alcohol alone (1.0 ml) caused spore death when used under the conditions of Example VI.

EXAMPLE VII

An experiment was conducted as described in Example VI above, but substituting 0.25 ml of acetic acid for formic acid. In this case the calculated partial pressure of peracetic acid vapor was one torr. Sterilization was achieved as in VI above.

SPECIFIC EXAMPLES OF PERFLUORINATED EMBODIMENTS

Trifluoroperacetic acid is conveniently produced from commercial 30% hydrogen peroxide and trifluoroacetic anhydride. Its vapor, when generated and used according to the procedures of the subject invention has been found to be a very effective sterilant.

EXAMPLE VIII

Fifteen biological indicator strips sealed in glassine envelopes and containing about a million spores each were placed upright in a stainless spring holder inside of a 22.6 L sterilization chamber to which was attached by means of a valve an external 100 ml glass vaporization chamber. The chamber was evacuated to about 14 torr and maintained at room temperature throughout the experiment. A liquid mixture containing trifluoroperacetic acid was prepared in an attached vaporization chamber as follows. Trifluoroacetic anhydride (7.6 ml) was cooled in ice and 30% hydrogen peroxide (1.0 ml) was added dropwise. A vigorous reaction was evident. The product mixture, now containing the peracid, was placed in the vaporization chamber heated. After five minutes at room temperature a valve connecting the vaporization chamber to the evacuated sterilization chamber was opened and the vaporization chamber to 50° C. The pressure in the sterilization chamber quickly rose by 46 torr to 60 torr. Air was admitted to the sterilization chamber to increase the total pressure to 600 torr. After 24 hours at room temperature the sterilization chamber was opened and contents were incubated by standard methods as described previously. No bacterial growth was detected after seven days, showing that trifluoroperacetic acid vapor is an effective sterilizing agent, and that it can be generated and used conveniently under the conditions of the present invention.

EXAMPLE IX

A test load containing paper biological indicators as well as both ceramic and stainless steel penicylinders, all contained within glassine envelopes and inoculated with spores of test organisms, was placed in a 22.4 L sterilization chamber as in Example III. The system was maintained at 35° C. and evacuated to 2.0 torr.

Perfluoropropionic anhydride (10.5 ml) was admitted into an external 100 ml glass vaporization chamber while keeping the connecting valve to the sterilizer closed. Hydrogen peroxide (1.0 ml, 30%) was added dropwise, without cooling, to the anhydride. A vigorous exothermic reaction was observed, and sterilant vapor (largely perfluoroperpropionic acid) was allowed to pass to the sterilization chamber after each addition by briefly opening the connecting valve to prevent excessive pressure build up in the vaporizer. At the end of the addition the pressure in the sterilizer had increased by 23 torr. Air was admitted to raise the internal pressure in the sterilizer to 600 torr, and the systems was left at 35° C. for 18 hours. The load was then freed from residuals by evacuation and the various inoculated challenges incubated by standard methods. No bacterial growth was observed on paper spore strips, or on ceramic or stainless steel penicylinders, indicating effective sterilization.

EXAMPLE X

An experiment was conducted using conditions and techniques similar to those described in EXAMPLE IV above, but using 13.3 ml of perfluorobutyric anhydride and 1.0 ml of 30% hydrogen peroxide to generate perfluoroperbutyric acid vapor. In this instance the sterilization chamber pressure rose from an initial value of 1.0 torr to 20 torr. Air was again admitted to a final internal pressure of 600 torr, and the chamber maintained at 35° C. for 30 hours. Removal and incubation of various biological challenges contained in the load showed paper strips, ceramic penicylinders and suture loops to be sterilized by this process.

This completes the description of the preferred and alternate embodiments of the invention. Those skilled in the art may recognize other equivalents to the specific embodiment described herein which equivalents are intended to be encompassed by the claims attached hereto.

What is claimed is:

1. A process for sterilizing a load of items to be disinfected by exposure to peracid sterilant vapor, comprising the steps of:

(a) introducing a load comprising items to be disinfected into a sterilization chamber adapted to contain and confine a sterilizing atmosphere;

(b) introducing an amount of peracid sterilant vapor into the sterilization chamber at a pressure below atmospheric pressure;

(c) introducing a quantity of a non-interfering gas, the gas being of a type which does not interfere with the sterilization procedure, to increase the pressure in the chamber to a value above that at which the chamber was after the peracid sterilant vapor was introduced but below atmospheric pressure, and forming, with the peracid sterilization vapor, a sterilization atmosphere; and (d) exposing the load to the sterilization atmosphere for a desired period of time to sterilize the load.

2. The process of claim 1 wherein the sterilization chamber is connected to a vaporization chamber and wherein step (b) further comprises:

(e) generating the peracid sterilant vapor in the vaporization chamber and allowing it to pass into the sterilization chamber; and (f) maintaining the sterilization chamber at a pressure equal to or less than that of the vaporization chamber during introduction of the peracid sterilant vapor.

3. The process of claim 2 wherein the peracid is selected from the group consisting of peracetic acid (peroxyacetic acid), performic acid (peroxyformic acid), perpropionic acid (peroxypropionic acid), perfluoroperacetic acid, perfluoroperpropionic acid, perfluoroperbutyric acid, and mixtures thereof.

4. The process of claim 3 wherein the peracid vapor is generated in situ by evaporation from a solution thereof.

5. The process of claim 3 wherein the peracid vapor is generated in situ by chemical reaction.

6. The process of claim 2 wherein the peracid is selected from peracetic acid (peroxyacetic acid), performic acid (peroxyformic acid), perpropionic acid (peroxypropionic acid), and mixtures thereof and wherein the peracid is generated by evaporation from a solution thereof.

7. The process of claim 6 wherein the peracid is peracetic acid.

8. The process of claim 7 wherein the pressure during step (d) is maintained within the range of 50–650 torr.

9. The process according to claim 8 wherein the reduced pressure for vaporizing the peracid is below about 100 torr.

10. The process of claim 2 further comprising the step of:

(e) removing the sterilant vapor by vacuum after exposure of the load for the desired period of time.

11. The process of claim 10 including repeating any of steps (b)–(e) as desired.

12. The process of claim 10 wherein evacuation is followed by flushing the chamber with a gas.

13. The process of claim 2 including repeating any of steps (b)–(d) as desired.

14. The process of claim 2 wherein the non-interfering gas is air.

15. The process of claim 2 wherein the pressure during step (d) is maintained within the range of 50–650 torr.

16. The process of claim 15 wherein the chamber pressure during step (d) is about 600 torr.

17. The process according to claim 2 wherein the reduced pressure for vaporizing the peracid is below about 100 torr.

18. The process according to claim 17 wherein the pressure is less than about 10 torr.

19. The process according to claim 17 wherein the pressure is less than about 1 torr.

20. The process according to claim 2 wherein the amount of peracid sterilant vapor introduced into the sterilization chamber is enough to raise the total pressure therein by at least about 1 torr.

21. The process of claim 1 wherein the peracid is selected from the group consisting of peracetic acid (peroxyacetic acid), performic acid (peroxyformic acid), perpropionic acid (peroxypropionic acid), perfluoroperacetic acid, perfluoroperpropionic acid, perfluoroperbutyric acid, and mixtures thereof.

22. The process of claim 21 wherein the peracid vapor is generated in situ.

23. The process according to claim 21 wherein the peracid is peracetic acid.

24. The process according to claim 21 wherein the peracid is performic acid.

25. The process according to claim 21 wherein the peracid is perpropionic acid.

26. The process according to claim 21 wherein the peracid is a mixture of peracids.

27. The process according to claim 21 wherein the mixture includes performic, peracetic and perpropionic acids.

28. The process according to claim 21 wherein the mixture includes peracetic and perpropionic acids.

29. The process according to claim 21 wherein the mixture includes peracetic and performic acids.

30. The process according to claim 21 wherein the mixture includes performic and perpropionic acids.

31. The process according to claim 21 wherein the peracid is a perfluorinated peracid.

32. The process according to claim 31 wherein the perfluorinated acid is selected from the group consisting of perfluoroperacetic acid, perfluoroperpropionic acid, perfluoroperbutyric acid and mixtures thereof.

33. The process of claim 1 wherein the peracid vapor is generated in situ.

34. The process of claim 1 further comprising the step of:

(e) removing the sterilant vapor by vacuum after exposure of the load for the desired period of time.

35. The process of claim 34 including repeating any of steps (b)–(e) as desired.

36. The process of claim 34 wherein evacuation is followed by flushing the chamber with a gas.

37. The process of claim 1 including repeating any of steps (b)–(d) as desired.

38. The process of claim 1 wherein the non-interfering gas is air.

39. The process of claim 1 wherein the pressure during step (d) is maintained within the range of 50–650 torr.

40. The process of claim 39 wherein the chamber pressure during step (d) is about 600 torr.

41. The process according to claim 1 wherein the amount of sterilant vapor introduced is defined in terms of partial pressure, the maximum amount being limited by its vapor pressure but greater than about 1 torr.

42. The process according to 41 wherein the partial pressure is about 10–15 torr.

43. A process for sterilizing a load of items to be sterilized by exposure to peracid sterilant vapor, comprising the steps of:

(a) introducing a load comprising items to be sterilized into a sterilization chamber adapted to contain and confine a sterilizing atmosphere;

(b) generating an amount of peracid sterilant vapor in a manner such that it is introduced into the cterilization chamber at a pressure below atmospheric pressure, wherein the peracid is selected from the group consisting of peracetic acid (peroxyacetic acid), performic acid (peroxyformic acid), perpropionic acid (peroxypropionic acid), perfluoroperacetic acid, perfluoroperpropionic acid, perfluoroperbutyric acid, and mixtures thereof;

(c) introducing a quantity of a non-interfering gas, the gas being of a type which does not interfere with the sterilization procedure, to increase the pressure in the chamber to a value from about 50 to 650 torr but above that at which the chamber was after the peracid sterilant vapor was introduced but below atmospheric pressure, and forming, with the peracids sterilization vapor, a sterilization atmosphere;

(d) exposing the load to the sterilization atmosphere for a desired period of time to sterilize the load; and (e) removing the sterilant vapor by vacuum after exposure of the load for the desired period of time.

44. The process of claim 43 including repeating any of steps (b)–(e) as desired.

45. The process of claim 43 including the step of removing liquid residue from the peracid sterilant vapor prior to introducing it into the sterilization chamber.

46. The process of claim 43 wherein evacuation is followed by flushing the chamber with a gas.

47. The process of claim 43 wherein the partial pressure of the peracid vapor after step (b) is 10–15 torr.

48. The process according to claim 43 wherein the reduced pressure for vaporizing the peracid is below about 100 torr.

49. A process for sterilizing a load of items to be sterilized by exposure to peracid sterilant vapor, comprising the steps of:

(a) introducing a load comprising items to be sterilized into a sterilization chamber adapted to contain and confine a sterilizing atmosphere wherein the sterilization chamber is connected to a vaporization chamber;

(b) generating the peracid sterilant vapor in the vaporization chamber maintained at a pressure below atmospheric and allowing it to pass into the sterilization chamber;

(c) maintaining the sterilization chamber at a pressure equal to or less than that of the vaporization chamber during introduction of the peracid sterilant vapor;

(d) wherein the peracid is selected from the group consisting of peracetic acid (peroxyacetic acid), performic acid (peroxyformic acid), perpropionic acid (peroxypropionic acid), perfluoroperacetic acid, perfluoroperpropionic acid, perfluoroperbutyric acid, and mixtures thereof;

(e) introducing a quantity of a non-interfering gas, the gas being of a type which does not interfere with the sterilization procedure, to increase the pressure in the chamber to a value between about 50 and 650 torr but above that at which the chamber was after the peracid sterilant vapor was introduced but below atmospheric pressure, and forming, with the peracid sterilization vapor, a sterilization atmosphere; and (f) exposing the load to the sterilization atmosphere for a desired period of time to sterilize the load; and (g) removing the sterilant vapor by vacuum after exposure of the load for the desired period of time.

50. The process of claim 49 including repeating any of steps (b)–(e) as desired.

51. The process of claim 49 including the step of removing liquid residue from the peracid sterilant vapor prior to introducing it into the sterilization chamber.

52. The process of claim 49 wherein evacuation is followed by flushing the chamber with a gas.

53. The process of claim 49 wherein the partial pressure of the peracid vapor after step (b) is 10–15 torr.

54. The process according to claim 49 wherein the reduced pressure for vaporizing the peracid is below about 100 torr.

* * * * *